United States Patent [19]

Asai et al.

[11] Patent Number: 5,935,943
[45] Date of Patent: Aug. 10, 1999

[54] INSECTICIDAL COMPOSITION

[75] Inventors: Takehito Asai, Kawasaki; Kenya Okumura, Tokyo; Toshiyasu Shizawa, Yokohama, all of Japan

[73] Assignee: Sankyo Company, Limited, Tokyo, Japan

[21] Appl. No.: 08/926,372

[22] Filed: Sep. 9, 1997

[30] Foreign Application Priority Data

Sep. 11, 1996 [JP] Japan .................................. 8-240118
May 16, 1997 [JP] Japan .................................. 9-126988

[51] Int. Cl.$^6$ .......................... A01N 31/14; A01N 37/00; A01N 43/64; A01N 55/00
[52] U.S. Cl. .......................... 514/63; 514/383; 514/511; 514/514; 514/515; 514/721
[58] Field of Search .................. 514/514, 515, 514/721, 511, 383, 63

[56] References Cited

FOREIGN PATENT DOCUMENTS 46-34420 10/1971 Japan .
3-128305 5/1991 Japan .
7-69819 3/1995 Japan .
7-138114 5/1995 Japan .

OTHER PUBLICATIONS

S. Asada, "Studies on Synergistic Effects of Pyrethroids with their Synergists", Osaka Shirutsu Daigaku Igaku Zasshi, vol. 20, 1971, pp. 337–359; and copy of C.A. 84485n, vol. 77, No. 13, 1972.

Tomlin, The Pesticide Manual, 10th Ed. pp. 418–419.

Primary Examiner—Allen J. Robinson
Attorney, Agent, or Firm—Frishauf, Holtz, Goodman, Langer & Chick, P.C.

[57] ABSTRACT

The presence of isobornyl thiocyanoethyl ether exerts a synergistic effect on the insecticidal activity against harmful wood eating insects of certain known insecticides selected from the group consisting of imidacloprid, phenyl pyrazole insecticides, pyrethroid insecticides and non-ester pyrethroid insecticides.

17 Claims, No Drawings

INSECTICIDAL COMPOSITION

BACKGROUND OF THE INVENTION

The present invention relates to a novel insecticidal composition for the eradication of harmful wood eating insects and comprising a known insecticide in admixture with isobornyl thiocyanoethyl ether (referred to herein as "IBTE").

Wood eating insects, such as termites, powderpost beetles (Lyctidae), lesser grain borers (Bostrichidae), drugstore beetles (Anobiidae), and longhorn beetles (Cerambycidae), cause considerable economic loss in many parts of the world. Although many different compounds have been proposed for use in their eradication, none has found complete acceptance for various reasons.

Traditionally, the active ingredient used for exterminating harmful wood eating insects such as those referred to above has been an inorganic compound (such as arsenic, arsenic pentoxide, arsenic trioxide, sodium hydrogen arsenate, chrome oxide, potassium dichromate, sodium dichromate, copper carbonate hydroxide, copper chloride, copper sulfate, sodium fluoride, ammonium fluoride, sodium silicofluoride, sodium borofluoride, boric acid or borax) or an organochlorine compound, such as chloronaphthalene, DDT, BHC, linden, dieldrin or chlordane. These compounds are frequently used because of their excellent stability and residual effect in wood and their low cost.

However, these compounds are highly toxic, and organochlorine compounds, in particular, are stable in the environment, for example in the soil. They are also very persistent in the human and animal body, and so, once they have entered the food chain, for example in the fat in fish or shellfish, they remain in the ecosystem, where their presence has become a problem. The manufacture, sale, import, and the like of these compounds are restricted in many countries, and most of them are prohibited from being used.

In place of these compounds, organophosphorus compounds, such as chlorpyrifos, pyridaphenethion, phoxim, fenitrothion, and chlorvinphos, and carbamate compounds, such as propoxur, fenobcarb, and carbaryl, have been used as agents for exterminating harmful wood eating insects.

However, organophosphorus compounds and carbamate compounds have the disadvantages that they have unpleasant odors, and that they are highly toxic, unstable to alkalis, unstable to soil bacteria and unstable to sunlight. Moreover, they must be used at a relatively high concentration (1% or more). Microcapsulation and similar procedures have been attempted to overcome these disadvantages, but this results in the problem of higher cost.

Recently, pyrethroid compounds, such as allethrin or permethrin, pyrethroid-like compounds, such as etofenprox. or silafluofen, and nicotinic acid compounds bound to nitroimidazolidylidene amine, such as imidacloprid, which have a chemical structure completely different from those of the forgoing compounds, have been used as agents for exterminating harmful wood eating insects. These pyrethroid compounds, pyrethroid-like compounds and imidacloprid are highly effective but have the disadvantage of high cost.

Japanese Patent Application Laid-Open No. Hei-7-69819 discloses the use of isobornyl thiocyanoalkyl ethers, including IBTE, for exterminating house dust mites, such as Acaridaes. Further, Japanese Patent Application Laid-Open No. Sho-46-34420 discloses that IBTE has an insecticidal effect on harmful insects such as flies, mosquitoes and cockroaches. However, IBTE is not been known to be effective for exterminating harmful wood eating insects such as termites. Indeed, as is shown hereafter, by itself, it has very little effect on such insects.

BRIEF SUMMARY OF THE INVENTION

It is an object of the present invention to develop an insecticidal composition which is preferably both inexpensive and has a powerful insecticidal activity against harmful wood eating insects, such as termites, which can cause severe damage to buildings.

We have now surprisingly found that a composition comprising a mixture of various known insecticidal compounds with IBTE exhibits a synergistic effect. Thus, it is possible to achieve a high insecticidal effect, whilst using far lower amounts of the expensive insecticides in combination with the inexpensive IBTE, which, by itself, exhibits no such activity against harmful wood eating insects.

Thus, the present invention provides an insecticidal composition having insecticidal activity against harmful wood eating insects and comprising effective amounts of at least one of the known insecticides listed below in combination with IBTE.

DETAILED DESCRIPTION OF INVENTION

Isobornyl thiocyanoethyl ether (IBTE), which is used in the present invention may be represented by the following formula (I):

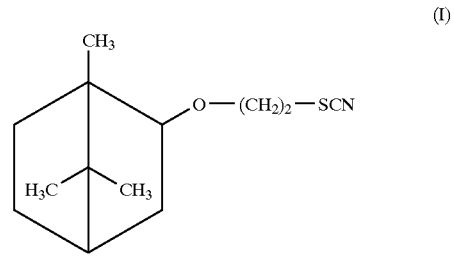

This compound is known to be effective against harmful insects, such as house flies, cattle flies, mosquitoes, fleas, lice, ants, moths, cockroaches, and bedbugs, and against mites, such as the Acaridae, and house dust mites.

The known insecticides used in the present invention are selected from the group consisting of imidacloprid, phenyl pyrazole insecticides, pyrethroid insecticides and non-ester pyrethroid insecticides.

Imidacloprid, which has the IUPAC name 1-(6-chloro-3-pyridylmethyl)-N-nitroimidazolidin-2-ylidene amine, may be represented by the following formula (II):

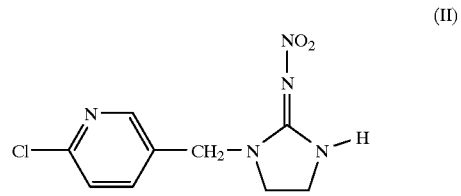

This compound is known to demonstrate a strong insecticidal activity at a low dosage against harmful insects of the order Hemiptera (e.g. plant hoppers, leaf hoppers and aphids), harmful insects of the order Coleoptera (e.g. rice leaf beetles and weevils), harmful insects of the order Thysanoptera (e.g. thrips) and on some harmful insects of the order Lepidoptera. It is, accordingly, registered and used as an insecticide for the treatment of rice in paddy fields, as well as for vegetables, fruit trees, and the like. Recently, imidacloprid has been further proposed for use as an agent for exterminating harmful wood eating insects because it has an excellent and powerful insecticidal activity against such insects.

An example of a phenyl pyrazole insecticide is fipronil, which has the IUPAC name (±)-5-amino-1-(2,6-dichloro-α, α,α-trifluoro-p-tolyl)-4-trifluoromethylsulfinylpyrazole-3-carbonitrile, and which may be represented by the following formula (III):

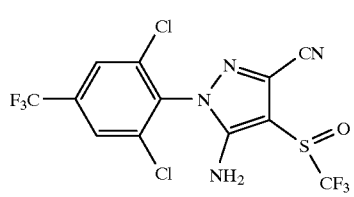

(III)

This compound, which is very expensive, is used primarily as an acaricide, and has not been used for the control of harmful wood eating insects.

Pyrethroid compounds that can be used in the present invention are compounds having a cyclopropane carboxy group. Examples of pyrethroid insecticides include allethrin, permethrin, cypermethrin, phenothrin, cyphenothrin, fenpropathrin, deltamethrin, tralomethrin and fenvalerate. These insecticide compounds are effective for exterminating sanitary insect pests and/or agriculturally harmful insects. They are structurally modified by synthetic chemistry from naturally occurring pyrethrins, which are present in pyrethrum flowers.

Preferred pyrethroid insecticides include allethrin and permethrin.

Allethrin has the IUPAC name (RS)-3-allyl-2-methyl-4-oxocyclopent-2-enyl (1RS,3RS;1RS,3SR)-2,2-dimethyl-3-(2-methylprop-1-enyl)cyclopropanecarboxylate and may be represented by the following formula (IV):

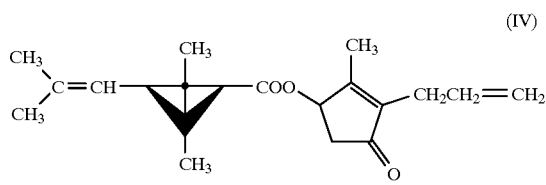

(IV)

Permethrin has the IUPAC name 3-phenoxybenzyl(1RS, 3RS;1RS,3RS)-3-(2,2-dichlorovinyl)-2,2-dimethylcyclopropanecarboxylate and may be represented by the following formula (V):

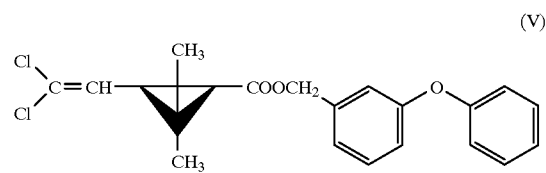

(V)

The non-ester pyrethroids are pyrethroid-like compounds which are similar to pyrethroid compounds. These compounds are free of a cyclopropane carboxy group, and examples of such compounds include etofenprox and silafluofen. These insecticidal compounds are effective for exterminating sanitary insect pest and/or agriculturally harmful insects. They, too, may be prepared by structural modification by synthetic chemistry of naturally occurring pyrethrins which are present in pyrethrum flowers.

Preferred non-ester pyrethroid insecticides include etofenprox and silafluofen.

Silafluofen has the IUPAC name (4-ethoxyphenyl)[3-(4-fluoro-3-phenoxyphenyl)propyl](dimethyl)silane and may be represented by the following formula (VI):

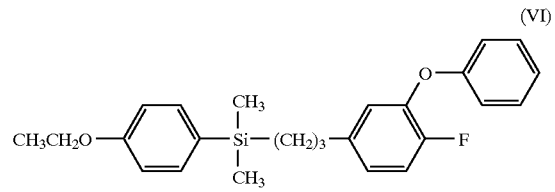

(VI)

Etofenprox has the IUPAC name 2-(4-ethoxyphenyl)-2-methylpropyl 3-phenoxybenzyl ether and may be represented by the following formula (VII):

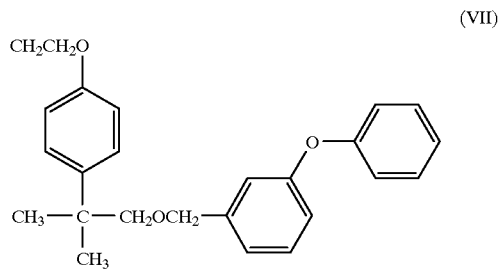

(VII)

Of the insecticides listed above, we prefer imidacloprid, allethrin, etofenprox, or silafluofen, more preferably, imidacloprid and pyrethroid-like compounds, most preferably imidacloprid or etofenprox.

We have surprisingly found that, when IBTE and one or more of these known insecticides are used together in suitable amounts, the resulting combination has a higher insecticidal activity against harmful wood eating insects and a higher inhibitory activity to prevent termites from making pores in soil, at a lower concentration than when either component was used alone, that is, we have found an excellent synergistic effect.

The ratio of IBTE to the above insecticide in the composition of the present invention is preferably in the range of from 1:1 to 10:1, more preferably from 3:1 to 5:1, and most preferably about 5:1. In the case of a mixture of IBTE and imidacloprid, a preferred ratio may be from 1:1 to 9:1. The composition of the present invention may be used in various forms as necessary. For example, it may be used as oil solution, an emulsion, a wettable powder, a flowable composition, a microcapsule suspension, a powder, granules, or a coating agent. A suitable adjuvant (such as a solvent, an emulsifying agent, or a dispersant) may, if desired, be included for use in this case.

Further, the insecticidal composition of the present invention can be used in combination (by blending) with such organic iodine type agents as IF-1000, sanplas, troysanpolyphase, and the like; triazole type agents such as azaconazole, propiconazole, tebuconazole, cyproconazole, and the like; or antiseptic antifungal agents such as thiabendazole, dichlofluanid, xylazane-A1, xylazane-B, and the like so as to improve its efficacy.

The concentration of the active component in the composition of the present invention in practical use is preferably in the range of from 0.05 to 1.5% by weight as (IBTE+the insecticidal compound).

The invention is further illustrated by the following non-limiting Examples, which show compositions of the present invention and the efficacy of the combination of active compounds of the present invention.

EXAMPLE 1

A solution of each of the following insecticides, either alone or in combination with IBTE in the specified proportion by weight, in acetone was applied to Formosan subterranean termites in a predetermined amount per termite, and the mortality rate of the termites was examined after 24 hours at 26±1° C.

In each case, 2 groups were used with each treatment group having 10 termites.

The results are shown in Table 1.

TABLE 1

| Insecticide | | Mortality rate of termites (%) | | | | |
|---|---|---|---|---|---|---|
| | Amount | Weight ratio of insecticide:IBTE*[1] | | | | |
| Name | ($10^{-3}$ μg) | 0:0 | 0:1 | 1:0 | 1:1 | 1:3 | 1:5 |
| Imidacloprid | 0.28 | | | 50 | 65 | 80 | 90 |
| | 0.40 | | | 50 | 80 | 90 | 100 |
| | 0.56 | | | 80 | 90 | 100 | 100 |
| Allethrin | 20.0 | | | 30 | 55 | 80 | 90 |
| | 30.0 | | | 55 | 90 | 95 | 100 |
| | 40.0 | | | 75 | 95 | 100 | 100 |
| Etofenprox | 5.0 | | | 15 | 80 | 90 | 95 |
| | 7.0 | | | 10 | 100 | 100 | 100 |
| | 10.0 | | | 45 | 100 | 100 | 100 |
| Silafluofen | 5.0 | | | 0 | 45 | 90 | 100 |
| | 7.0 | | | 50 | 80 | 100 | 100 |
| | 9.0 | | | 90 | 100 | 100 | 100 |
| IBTE alone | 150.0 | | 0 | | | | |
| Control | | 0 | | | | | |

*[1]The ratio is relative to the amount of insecticide. Thus, for example, where the amount of imidacloprid is $0.28 \times 10^{-3}$ μg and the ratio is 1:1, the amount of IBTE is also $0.28 \times 10^{-3}$ μg.

EXAMPLE 2

A solution of each of the following insecticides, either alone or in combination with IBTE in the specified proportion by weight, in acetone was applied to previously air-dried soil, and then the soil was air-dried and mixed sufficiently so that the soil contained the insecticide or mixture at a predetermined concentration per unit weight. A 5 cm layer of the soil was then placed into a glass tube of about 1.5 cm inner diameter, and distilled water was added thereto, to adjust the degree of water saturation in the soil to about 50%. This glass tube was connected at one end to a vessel containing 40 worker termites and at the other end to a vessel containing wet wood powder. It was left for 4 days at 26±1° C. in the dark and the degree to which the termites were inhibited from penetrating through the soil was examined. Each experiment was carried out in duplicate.

The results are shown in Table 2.

The criteria for evaluating the degree of inhibition are as follows:

+: The termites were inhibited from penetrating in both test groups.

±: The termites were inhibited from penetrating in only 1 group.

−: The termites were not inhibited from penetrating in either group.

TABLE 2

| Insecticide | | Degree of inhibition of pore making Mixing ratio of | | | | | |
|---|---|---|---|---|---|---|---|
| Name | Concentration in soil(ppm) | test insecticide compound:IBTE*[1] | | | | | |
| | | 0:0 | 0:1 | 1:0 | 1:1 | 1:3 | 1:5 |
| Imidacloprid | 30.0 | | | + | + | + | + |
| | 15.0 | | | − | + | + | + |
| Etofenprox | 80.0 | | | + | + | + | + |
| | 40.0 | | | − | + | + | + |
| Permethrin | 80.0 | | | + | + | + | + |
| | 40.0 | | | − | − | + | + |
| IBTE | 200.0 | | − | | | | |
| Cont. | 0 | − | | | | | |

EXAMPLE 3

Wood was surface treated with a 100 ml/m² solution of each insecticide, either alone or in combination with IBTE in the specified proportion by weight. It was then air-dried and used as a test sample. This test sample and 10 insects of powderpost beetle (Lyctidae) were introduced into a beaker which was then left in a thermostatic chamber at 25° C. under 70% humidity for a predetermined period. After the insects had laid eggs on the test sample, the insects were removed. The number of insects hatched from the eggs on each test sample were counted. 3 groups (Group 1, Group 2 and Group 3 in the following Table) were used for each test. The results are shown in Table 3.

TABLE 3

| Insecticide | | Number of Hatched Insects | | | |
|---|---|---|---|---|---|
| Name | Concentration for Treatment(%) | Group 1 | Group 2 | Group 3 | Average |
| Imidacloprid | 0.02 | 3 | 6 | 4 | 4 |
| | 0.04 | 1 | 0 | 0 | 0 |
| Imidacloprid + IBTE | 0.02 + 0.02 | 1 | 2 | 2 | 2 |
| | 0.02 + 0.06 | 0 | 0 | 0 | 0 |
| | 0.02 + 0.10 | 0 | 0 | 0 | 0 |
| Allethrin | 0.05 | 8 | 7 | 8 | 8 |
| | 0.10 | 2 | 2 | 3 | 3 |
| Allethrin + IBTE | 0.05 + 0.05 | 5 | 3 | 4 | 4 |
| | 0.05 + 0.15 | 2 | 2 | 1 | 2 |
| | 0.05 + 0.25 | 0 | 0 | 0 | 0 |
| Permethrin | 0.04 | 6 | 4 | 7 | 6 |
| | 0.08 | 1 | 0 | 0 | 0 |
| Permethrin + IBTE | 0.04 + 0.04 | 5 | 5 | 3 | 4 |
| | 0.04 + 0.12 | 3 | 3 | 1 | 2 |
| | 0.04 + 0.20 | 0 | 0 | 0 | 0 |
| Etofenprox | 0.04 | 3 | 4 | 3 | 3 |
| | 0.08 | 0 | 0 | 0 | 0 |
| Etofenprox + IBTE | 0.04 + 0.04 | 1 | 1 | 2 | 1 |
| | 0.04 + 0.12 | 2 | 0 | 1 | 1 |
| | 0.04 + 0.20 | 0 | 0 | 1 | 0 |
| Silafluofen | 0.025 | 7 | 8 | 5 | 7 |
| | 0.05 | 2 | 0 | 3 | 2 |
| Silafluofen + IBTE | 0.025 + 0.025 | 4 | 4 | 5 | 4 |
| | 0.025 + 0.075 | 1 | 0 | 1 | 1 |
| | 0.025 + 0.125 | 0 | 0 | 0 | 0 |
| IBTE | 0.75 | 12 | 10 | 11 | 11 |
| | 1.5 | 2 | 1 | 1 | 1 |
| Cont. | 0 + 0 | 13 | 16 | 15 | 15 |

EXAMPLE 4

A filter paper treated with an acetone solution containing one of the following insecticides, either alone or in combination with IBTE in the specified proportion by weight, at the concentration specified in the following Table was air-dried. Each filter paper was placed into a test tube, and 10 worker termites were released into each test tube. The test tubes were then placed in a room at 26±1° C. After 4 days, the percentage kill was assessed for each treatment group. The experiment was carried out in duplicate for each compound or mixture. The results are shown in Table 4.

TABLE 4

| Insecticide | | Mortality rate of termites (%) | | | | | |
|---|---|---|---|---|---|---|---|
| | Concentration | Weight ratio of insecticide:IBTE*1 | | | | | |
| Name | (ppm) | 0:0 | 0:1 | 1:0 | 1:1 | 1:3 | 1:5 |
| Fipronil | 14 | | | 65 | 100 | 100 | 100 |
| | 10 | | | 50 | 100 | 100 | 100 |
| | 7 | | | 15 | 70 | 100 | 100 |
| | 5 | | | 10 | 70 | 90 | 100 |
| Etofenprox | 200 | | | 75 | 100 | 100 | |
| | 100 | | | 5 | 70 | 90 | 100 |
| Silafluofen | 150 | | | 45 | 65 | 100 | |
| | 75 | | | 15 | 35 | 60 | 85 |
| Allethrin | 100 | | | 5 | 40 | 100 | |
| IBTE alone | 3000 | | 0 | | | | |
| Control | | 0 | | | | | |

The above results demonstrate that the presence of IBTE, which, alone, has no effect on termites or similar harmful wood-eating insects, results in a real synergistic effect.

We claim:

1. An insecticidal composition having insecticidal activity against harmful wood-eating insects, comprising synergistic effective amounts of (i) at least one insecticide selected from the group consisting of etofenprox and silafluofen in combination with (ii) isobornyl thiocyanoethyl ether.

2. The composition of claim 1, wherein said insecticide is etofenprox.

3. The composition of claim 1, wherein said insecticide is silafluofen.

4. The composition of claim 1, wherein the weight ratio of said isobornyl thiocyanoethyl ether to said insecticide is from 1:1 to 10:1.

5. The composition of claim 1, wherein the weight ratio of said isobornyl thiocyanoethyl ether to said insecticide is from 3:1 to 5:1.

6. The composition of claim 1, wherein the weight ratio of said isobornyl thiocyanoethyl ether to said insecticide is about 5:1.

7. The composition of claim 2, wherein the weight ratio of said isobornyl thiocyanoethyl ether to said insecticide is about 5:1.

8. The composition of claim 3, wherein the weight ratio of said isobornyl thiocyanoethyl ether to said insecticide is about 5:1.

9. The composition of claim 1, which further comprises an effective amount of an organic iodine insecticide, a triazole insecticide, or an antiseptic antifungal insecticide.

10. The composition of claim 1, which further comprises an effective amount IF-1000, sanplas, troysanpolyphase, azaconazole, propiconazole, tebuconazole, cyproconazole, thiabendazole, dichlofluanid, xylazane-A1 or xylazane-B.

11. A method of eradicating harmful wood-eating insects by applying to the wood-eating insects or to soil or wood a composition comprising synergistic effective amounts of (i) at least one insecticide selected from the group consisting of etofenprox and silafluofen, in combination with (ii) isobornyl thiocyanoethyl ethyl.

12. The method of claim 11, wherein the insecticide is etofenprox.

13. The method of claim 11, wherein said insecticide is silafluofen.

14. The method of claim 11, wherein the weight ratio of said isobornyl thiocyanoethyl ether to said insecticide is 1:1 to 10:1.

15. The method of claim 11, wherein the weight ratio of said isobornyl thiocyanoethyl ether to said insecticide is 1:1 to 9:1.

16. The method of claim 11, wherein the weight ratio of said isobornyl thiocyanoethyl ether to said insecticide is 3:1 to 5:1.

17. The method of claim 11, wherein the wood-eating insects are selected from the group consisting of termites and powderpost beetles.

* * * * *